Figure 1:
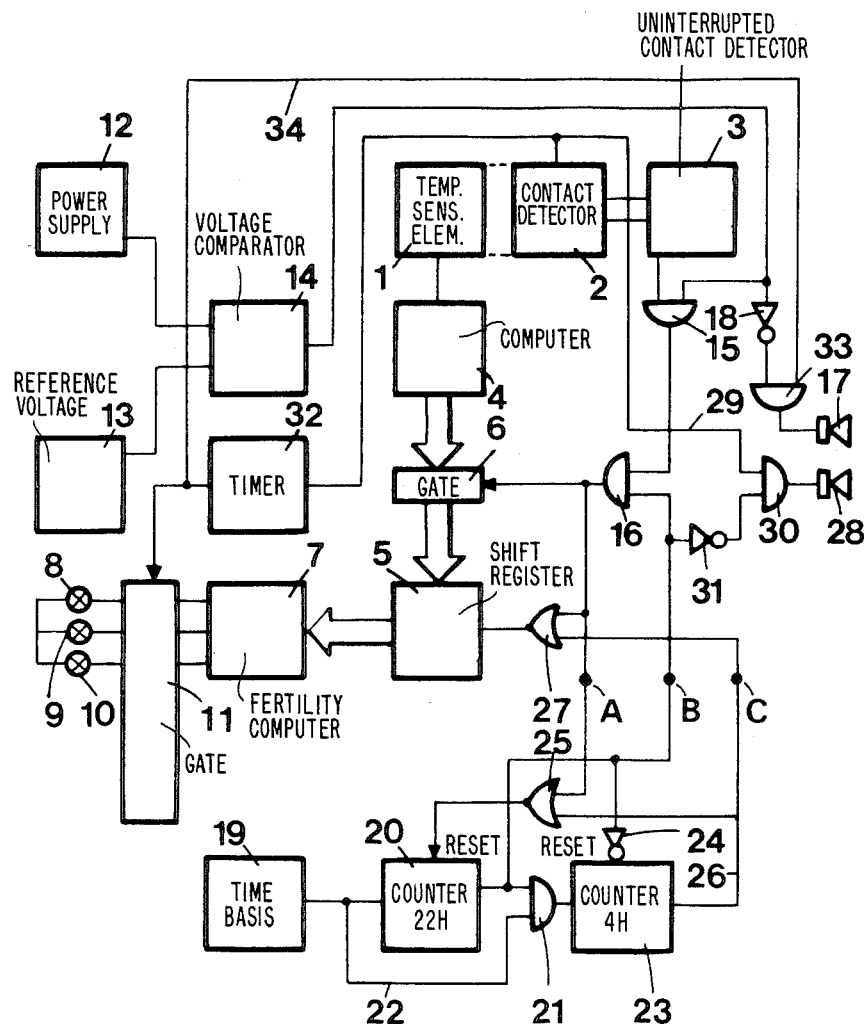

United States Patent [19]

Aeschlimann

[11] Patent Number: 4,752,880

[45] Date of Patent: Jun. 21, 1988

[54] APPARATUS FOR ASSESSING THE CURRENT STATE OF FERTILITY OF A PERSON

[75] Inventor: Claude Aeschlimann, Thônex, Switzerland

[73] Assignee: Bioself International Inc., Nassau, The Bahamas

[21] Appl. No.: 15,546

[22] Filed: Feb. 13, 1987

Related U.S. Application Data

[63] Continuation of Ser. No. 662,999, filed as PCT CH84/00025 Feb. 17, 1984, published as WO84/03379, Aug. 30, 1984, abandoned.

[30] Foreign Application Priority Data

Feb. 24, 1983 [CH] Switzerland ............... 1050/83

[51] Int. Cl.$^4$ ............................................. G01K 7/00
[52] U.S. Cl. .................................... 364/415; 128/736
[58] Field of Search ............... 364/413, 415, 417, 557, 364/705–706; 128/736, 738

[56] References Cited

U.S. PATENT DOCUMENTS

| 4,148,304 | 4/1979 | Mull | 128/738 X |
| 4,151,831 | 5/1979 | Lester | 128/738 |
| 4,312,360 | 1/1982 | Conway et al. | 128/736 |
| 4,367,527 | 1/1983 | Desjacques | 364/413 |
| 4,370,727 | 1/1983 | Bellet | 364/705 |
| 4,377,171 | 3/1983 | Wada | 128/736 |
| 4,396,020 | 8/1983 | Wolff et al. | 128/738 |
| 4,443,851 | 4/1984 | Lin | 364/415 |
| 4,465,077 | 8/1984 | Schneider | 128/738 |
| 4,475,158 | 10/1984 | Elias | 364/413 |
| 4,488,560 | 12/1984 | Takamura | 128/738 |
| 4,530,366 | 7/1985 | Nessi et al. | 128/736 |
| 4,541,734 | 9/1985 | Ishizaka | 128/736 |
| 4,629,336 | 12/1986 | Ishizaka | 128/736 |

FOREIGN PATENT DOCUMENTS

| 8403379 | 8/1984 | PCT Int'l Appl. | 128/738 |
| 2045480 | 10/1980 | United Kingdom | 364/557 |

Primary Examiner—Jerry Smith
Assistant Examiner—Kimthanh Tbui
Attorney, Agent, or Firm—Trexler, Bushnell, Giangiorgi & Blackstone, Ltd.

[57] ABSTRACT

The transfer of the temperature of a body to a fertility calculator (7) is only authorized by the time controller (20, 23) when a first counter shows that a first preselected period of time (e.g., 22 hours) has elapsed since the previous temperature measure and when a second counter (23) shows that the temperature is being taken during a second preselected time interval (e.g. 4 hours) following the first period of time. Accordingly, only one measure can be made per day at approximately the same time, thereby eliminating the important problem encountered when the temperature is taken at irregular intervals.

10 Claims, 3 Drawing Sheets

APPARATUS FOR ASSESSING THE CURRENT STATE OF FERTILITY OF A PERSON

This application is a continuation of application Ser. No. 662,999, filed as PCT CH84/00025 on Feb. 17, 1984, published as W084/03379 on Aug. 30, 1984 and now abandoned.

Apparatus for indicating the state of fertility of a person during her ovulation cycler are known, which comprise an electric power supply, a thermal probe to be put into contact with the body of the person for measuring her temperature, preferrably her basal temperature, a fertility calculator, and display means of the state of fertility, controlled by said calculator (U.S. Pat. No. 4,151,831; European Pat. Nos. 0 022 060 and 0 031 251).

However, it is very important that the successive temperature measurements take place at fixed time, with a moderate margin, for example 24 hours plus or minus 2 hours. The known apparatus just referred to are based on the assumption that the users of them follow this time schedule strictly. But, in practice, it is quite possible that the temperature measurements will be made at time intervals departing, in one direction or the other, with an excessive margin, with the consequence that the calculation of the apparatus are falsified and as a result its indications as regards the state of fertility are wrong. It is known, in fact, that there is a daily rhythm of variation of the temperature of all persons, for example the temperature of a person in good health is always higher in the evening than in the morning. Measurements of temperature at irregular time intervals are causes of fallacious indications of the known apparatus.

In view to avoid the foregoing problem it has been suggested (U.S. Pat. Nos. 4,475,158, 4,530,366 and 4,396,020) to arrange the apparatus such that the temperature measurement is accepted by the apparatus, i.e., "validated", only if it takes place within a "time window" fixed in time and of a duration of, for example, 4 hours. Thus, the measurement will be validated, i.e., taken as a basis for calculations by the apparatus, if it takes place during the interval 24 plus or minus 2 hours, 24 hours being the constant interval between the middle of two such successive time windows.

However, this system of fixed windows has still drawbacks: rigidity for the user who is compelled to follow a fixed schedule or time table, as well as the possibility nevertheless of a signficant, and error-causing time difference between two successive measurements. In fact, if the window is of 4 hours duration, and one day the measurement is made exactly at the beginning of the window, the variation in the time of measurement the next day can be as great as 8 hours (twice the duration of a window). Such an important difference has a deleterious effect on the reliability of the apparatus.

The present invention has for an object to overcome all of the aforesaid drawbacks by providing a time window of constant duration and which is automatically adjustable in time, according to the time of the previous time measurement.

The invention relates to an apparatus according to claim 1.

OBJECTS AND SUMMARY OF THE PRESENT INVENTION

The present invention is aimed at overcoming the disadvantages of the known apparatus, and has for object an apparatus for assessing the current state of fertility of a person in accordance with claim 1.

THE DRAWINGS

Figure 2:
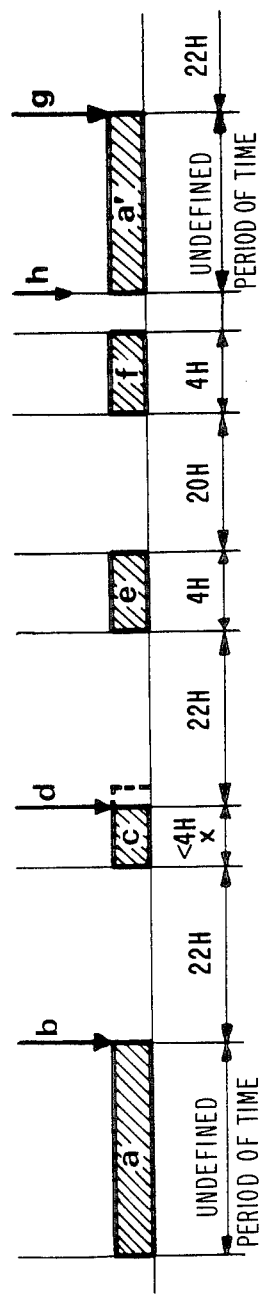
Figure 3:
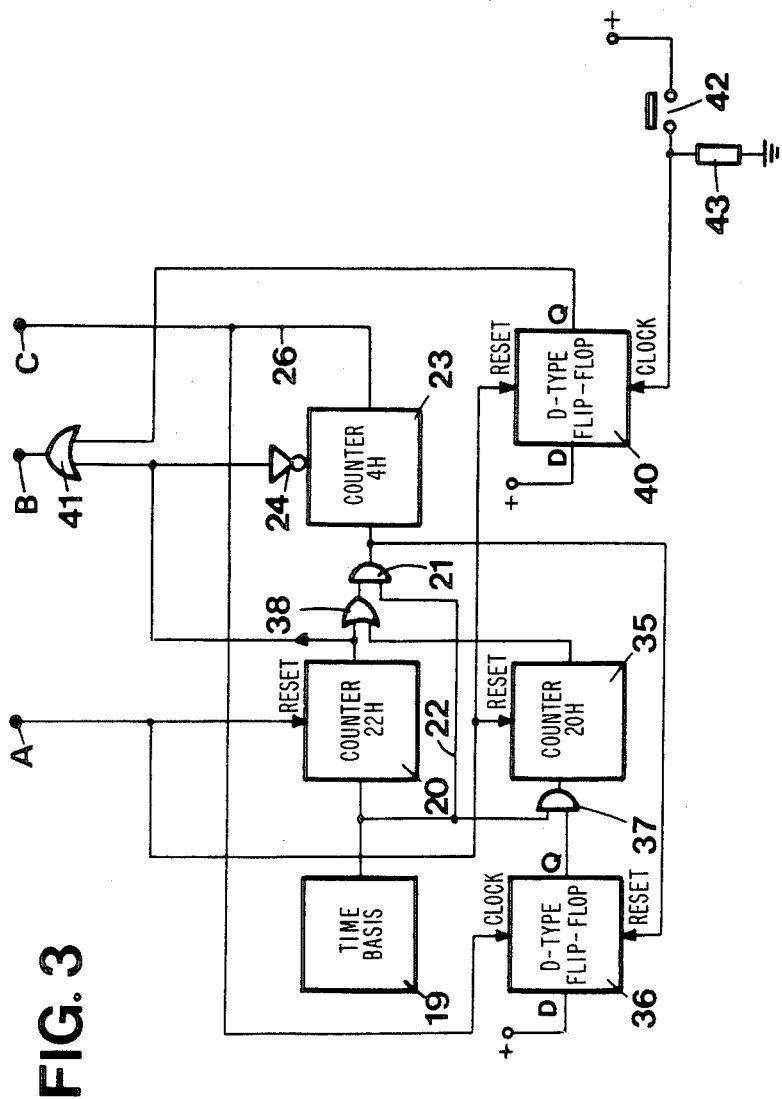

FIG. 1 of the appended drawings is a block diagram given by way of example of an embodiment of the invention, FIG. 2 is an explanatory diagram corresponding to a refined version of the embodiment of FIG. 1, FIG. 3 is a partial block diagram showing how the circuit of FIG. 1 should be modified to produce said version.

DETAILED DISCLOSURE OF THE ILLUSTRATED EMBODIMENTS

The apparatus comprises a temperature sensitive element 1 located inside a thermometric probe. To this element 1 is associated a contact detector 2. This detector can be located on the probe, or consist of a specific electric circuit associated with the temperature sensitive element and located inside the probe. To this contact detector 2 is further associated a contact controller 3, which has for function to check constantly from the moment when the detector 2 acknowledges that the probe is in contact with the body of the person whose temperature is to be taken, that this contact is maintained uninterrupted during a preselected length of time. The preselected length of time is choosen according to the thermal inertia of the probe and of the temperature sensitive element, so as to be sufficient to enable the temperature sensitive element 1 to reach the temperature of the body. The apparatus further comprises a thermometric computer 4 of a known type which converts the analog signals delivered by the temperature sensitive element 1 into digital data. This computer 4 transfers the calculated digital data to a shift register 5 through a gate 6 which therefore controls this transfer. 7 is a fertility computer which calculates from the body temperature taken regularly every 24 hours the state of fertility of a person, i.e. whether the probability of pregnancy is low, high or nil. It is well known that the probability of pregnancy is progressively modified during each ovulation cycle.

The fertility computer 7 is designed to actuate a readout system, consisting for example of three lights 8, 9 and 10 which indicate whether the probability of pregnancy is low, high or nil. A gate 11 is provided to restrict the functioning of the lights 8, 9 and 10 to when the user wishes to know her state of fertility, thus minimizing the power consumption of the apparatus. The gate 11 is controlled by the contact detector 2 through a timer 32 which limits the length of time during which the gate 11 can be opened.

The apparatus is further provided with a power supply 12 for supplying the memory voltage.

A reference voltage source 13 is also provided. It comprises for example, a Zener diode which derives this reference voltage from the power supply 12 itself. A voltage comparator 14 is further provided to check that the voltage from the power supply 12 is still adequate and has not fallen below a level where it can no longer be used. When the voltage is adequate, 14 authorizes the continued use of the apparatus. When the voltage becomes too low for the apparatus to operate correctly, the comparator 14 does not emit a continuation signal to the AND gate 15, thereby preventing the opening of the gate 6 and the transfer of the temperature. When the comparator 14 indicates that the voltage from the power supply is adequate and when at the same time the contact controller 3 indicates that the contact has remained uninterrupted for the selected length of time, the AND gate 15 opens for the passage of a signal to the AND gate 16. If however, the voltage comparator 14 finds that the power supply cannot be used any longer, a sonic warning device 17 is actuated through a logical inverter 18 and an AND gate 33, provided at the same time the timer 32 functions.

The apparatus comprises a quartz controlled time base 19 emitting constantly impulses, for example every second. A counter 20 controlled by the time base 19 counts time from 0 to 22 hours by using the impulses emitted by the time base 19. When the counter 20 has counted 22 hours, it opens the AND gate 21 which is also connected to the output of 19 by the conductor 22. The impulses emitted by 19 are then admitted through the gate 21 to another counter 23 which counts time for up to 4 hours.

When the counter 20 has counted 22 hours, it emits a signal to the inverter 24 which prevents the resetting of the counter 23 until reception of an appropriate signal. At the same time, this signal is received by the gate 16. If the gate 16 receives at the same time the signal from the counter 20 and a signal from the gate 15, the gate 6 is opened. At this moment, it is established by the controller 3 that the contact between the probe and the body has remained uninterrupted for the preselected length of time and that the measure is taking place in the right interval of time, i.e. 24 hours±2 hours. The temperature can then be recorded, i.e. the computer 4 can transfer the numerical value corresponding to the temperature to the shift register 5. Consequently, the fertility computer 7 can carry out a new set of calculations. When the gate 16 opens the gate 6, it opens at the same time the OR gate 25, whereby the counter 20 is reset. When the counter 20 is reest, its output changes from 1 to 0 and the counter 23 is reset through the inverter 24.

If no temperature measure is made during the 4 hours when the counter 23 counts, this counter sends a signal through 26 to the gate 25 to reset the counter 20. This sequence of events is observed if the user omits to take her temperature during the 4 hours authorized by the counter 23. The signal delivered by 26 is also received by the shift register 5 through the OR gate 27 to take into account the fact that one day has elapsed without the temperature being taken.

This OR gate 27 which controls the register 5 also allows the passage of a signal each time gate 6 is opened by the gate 16. A sonic warning device 28 is actuated when the contact detector has detected that the contact is established and when at the same time the counter 23 shows that the measure is being taken outside the authorized period of time. The warning system functions as follows: the contsct detector 2 sends a signal through 29 to the AND gate 30: at the same time; the counter 20 which was reset because the time interval of 4 hours has elapsed sends a signal which is received by the gate 30 through the inverter 31. When the two signals are received at the same time, by the AND gate 30, the warning device 28 is set off and the user is warned that the temperature measure was not accepted.

The apparatus described above functions as follows:

When the user applies the probe against her body, the detector 2 is actuated and in turn actuates the contact controller 3 and the timer 32, opens the gate 11 and actuates the readout system 8, 9 and 10 to indicate the current state of fertility. At the same time the timer 32 opens the gate 33 through the conductor 34. The voltage comparator 14 determines if the power supply is still in working condition. If not, the sonic warning device 17 is set off. If on the contrary, the power supply is in working condition the gate 33 prevents the sonic warning device 17 from being set off. When the control detector remains actuated, i.e. if the probe remains in contact with the body, the following process takes place: the contact controller 3 remains actuated, and if the counter 23 indicates that the measure is being taken within the authorized period of time, the gate 6 is opened by the gage 16. The gate 16 is open because the counter 20 has counted 22 hours and has not been reset and the counter 23 has not yet counted 4 hours. The numerical value of the temperature calculated by 4 is therefore transmitted to the shift register 5. The register 5 transmits the data it contains to a fertility computer 7. The new state of fertility is then determined which can be identical to the previous state or different. This determination can only be carried out if the gate 6 is open.

If the temperature is taken outside the 4 hours period counted by the counter 23, the temperature measure is not accepted through the gate 6. The signal from the counter 20 arrives through the inverter 31 to the gate 30, while the signal of the detector 2 arrives to this gate through the conductor 29.

The user can stop the above described process when she desires simply by removing the probe from her body. The action of the contact detector on the contact controller prevents the opening of the gate 15. The temperatures are not transmitted any more from 4 to 5 because the gate 6 remains closed. The user, when she wishes to know her state of fertility only needs to apply the probe on her body. When this information is given to her by the lights 8,9 and 10, she removes the probe from her body and the apparatus is automatically reset.

In one version of the invention the voltage comparator 14 is omitted and the state of fertility is given by acting on an external contactor without using the contact detector.

It can be advantageous to be warned by a sound or a light signal that the temperature measure is terminated. The warning device could simply be actuated by the signal transmitted through the gate 16 to the gate 6.

FIG. 2 describes two particular situations. In the first situation, the user has begun to use the apparatus, but has subsequently omitted to take her temperature. In the second situation, the user has travelled to a different longitude and wishes to take her temperature at the same local time as previously, for example in the early morning.

FIG. 3 shows how the apparatus of FIG. 1 should be modified to meet the requirements resulting from the two situations described above. In such a modified version of the apparatus, the part of the circuit of FIG. 1 located underneath the points A, B and C is replaced by the circuit shown in FIG. 3, the rest of the circuit remaining unaltered.

Let us first examine the diagram of FIG. 2. Time is represented on the horizontal axis. During a first period of time of undefined duration designated by the letter a in FIG. 2, the apparatus is not used. At the end of this undefined period of time a, the user proceeds to a first temperature measure at instant b. Immediately, the 22 hour counter 20 begins to function, i.e. to count the impulses delivered by the time base 19. When the 22 hours have elapsed, and as was explained previously, the 4 hour counter 23 is started. During this period of 4 hours (c in FIG. 3) a second temperature measure is made at instant d. The 22 hour counter 20 is thereby reset and begins to count time again for 22 hours. If during the following period e of 4 hours the temperature is taken as it normally should, the same process as described above is repeated. However, if for some reason the user omits to take her temperature during the 4 hour period e, then the apparatus must proceed to a correction so that the length of the following period be 20 hours instead of the normal 22 hours. If such a correction was not made, the following period would in fact last 26 hours instead of 24, and if the omission was repeated several times, the effect would be cumulative, which is contrary to the requirement that the temperature be taken regularly every 24 hours and during the same period of the day. It can be further seen on the diagram of FIG. 2 that the user omitted again to take her temperature in the 4 hour period f following the 20 hour period. In this case, the period f would be followed by another period of 20 hours. If the user had taken her temperature during the 4 hour period f, the following period would have been of 22 hours. The succession of events described corresponds to the first situation considered above.

The right hand side of the diagram illustrated the situation where the user has to change the time of the temperature to measure, for example when she has travelled to a different longitude where she is to remain for some time. The apparatus must then be reset by the user so as to be in the same condition as in the first period a, and designated by a' in FIG. 2. The apparatus is reest by using a circuit which will be described further. Once reset, the apparatus remains ready during an undetermined period of time for a first temperature reading g. From then, the apparatus is used again as previously from the instant b. The letter h indicates the moment when the apparatus was reset.

We shall now examine the circuit of FIG. 3 which is used to carry out the operations described above.

FIG. 3 shows that this circuit comprises a time base 19, a counter 20, a counter 23 and gates 21 and 24 as in the embodiment of FIG. 1. The following additional components have been included: a counter 35 controlled by the time base 19 for counting time to 20 hours, and a D-type flip-flop 36 controlling the counter 35 through an AND gate 37. The 4 hour counter 23 acts on the flip-flop 36 when the 4 hours have elapsed without the temperature being taken to open the AND gate 37. When the AND gate 37 is opened to the impulses from the time base 19, the 20 hour counter 35 begins to count. The counters 20 and 35 control an OR gate 38 which is further connected to the AND gate 21. This gate controls the 4 hour counter 23 when the two counters 20 and 35 count simultaneously. The continued functioning of the counter 20 is of no importance if the counter 35 functions, because the count of the counter 35 is terminated before that of the counter 20. Accordingly, when the counter 35 counts, it controls in conjunction with the time base 19, the transmission of impulses to the 4 hour counter 23, whereby the conditions corresponding to the letter f of FIG. 2 are realized.

The above process described with reference to FIG. 3 concerns the first situation schematically represented in FIG. 2 when the user has omitted once or several times to take her temperature. Quite obviously, if no such omission occurs, the circuit of FIG. 3 does not modify the functioning of the circuit of FIG. 1. To meet the requirements resulting from the second situation also schematically represented in FIG. 2, i.e. when the user has travelled to a different longitude, a D-type flip-flop 40 is provided which is reset when the gate 6 (FIG. 1) is opened by a signal delivered from the gate 16.

This same signal resets the counter 20 which immediately begins to count 22 hours. When the 22 hour count is reached, and as was described previously, the counter 23 begins to count 4 hours and the conditions illustrated in the diagram of FIG. 2 are resumed.

This flip-flop 40 controls an OR gate 41 which is also controlled by the 22 hour counter 20. The gate 41 is open when the 22 hour count is terminated or when the flip-flop 40 is activated. A switch 42 is also provided to start the apparatus after the user has travelled to a different longitude: she only needs to actuate this switch for a short moment. 43 is a polarisation resistance. The closing of the switch 42 resets the flip-flop 40 to state 1 thereby opening gate 41. The temperature can be taken then. At this stage, the apparatus is in the situation designated by the letter g in FIG. 2. Subsequently, the counters 20 and 23 will make certain that the temperature is taken regularly every 24 hours within the selected time limits.

For sake of completeness it should be mentioned that previously to the period of time designated by the letter a in FIG. 2, the apparatus was not provided with a power supply. The period a is initiated when the power supply is connected to the apparatus. This period a ends when the first temperature is taken (b in FIG. 2). Quite obviously, the period of time designated by the letter a' and which corresponds to the user travelling to a different longitude can recur as often as desired. The user is only required to actuate the switch 42. This switch is therefore used very seldom and only when the user travels to a different longitude.

The switch 42 and the resistance 43 could be eliminated. In this case the user would only have to remove the power supply 12 when travelling to a different longitude. The apparatus would then be in the state a. Buffer batteries (not illustrated in the drawings) are then used to keep the data in the memories, in accordance with known practices.

The logic circuits of FIGS. 1 and 3 are hard-wired logic circuits. They could easily be replaced by programmable logic circuits having the same function, i.e. by a microprocessor.

What is claimed is:

1. Apparatus for indicating the present state of fertility of a person during her ovulation cycle, of the kind comprising an electric power supply (12), a thermal probe (1) for making temperature measurements and for generating analog signals corresponding to the temperature measurements, a calculator converter (4) for converting into electric digital signals, the analog signals generated by the probe (1) when put into contact with the body of the person, a fertility calculator (7) responsive to said calculator converter (4), for providing electric signals indicating the state of fertility of the person, and a time controller (20, 23) for authorizing and validating a given temperature measurement at a given time each day only if said given time is within a daily time window of fixed duration (e.g., of 4 hours), characterized in that said time controller comprises means (14-23) for assigning on each day a position in time of the time window in dependence upon the given time that the temperature measurement was authorized and validated on the previous day for thus automatically resetting the position of the time window in the event that the time of day of the temperature measurement changes from day to day within the window; and further characterised in that the means for assigning, each day, the position in time of the time window are arranged for fixing the beginning of the time window of each day at 24 hours less a predetermined proportion of the duration of the time window following the given time of the previous day's authorized and validated measurement.

2. Apparatus according to claim 1, characterized in that said predetermined proportion comprises one-half.

3. Apparatus according to claim 2, characterized in that it further comprises means for assuring that, in case of omission of at least one daily temperature measurement, temperature measurements on subsequent days continue on the basis of the temperature measurements previous to and following the day or days on which measurements are omitted.

4. Apparatus according to claim 2, characterized in that it is further provided with means for assuring that, if the electric power supply becomes non-operating during a short duration (for example 90 seconds), on the one hand the data memorized in the apparatus are preserved, and, on the other hand, the next temperature measurement following said short duration acts as a new start, independent of the last previous measurement before said short duration for the automatic assignment of the position in time of the time window of the following day, to enable the user to adapt to a change of time zone.

5. Apparatus according to claim 1 and comprising a controller of the electric power supply (12), a detector (2) of contact of the probe (1) with the body of the person, for initiating operation of the time controller (20, 23), and a controller (3) of non-interrupted contact of the probe (1) with the body, for authorizing the temperature measurement only if the contact of the probe with the body is non-interrupted during a predetermined time duration sufficient to enable the probe, due to its thermal inertia, to reach the temperature to be measured.

6. An apparatus according to claim 5, characterized in that it further comprises means (13, 14) for controlling the voltage of the power supply (12) by the comparison of this voltage (14) with a reference voltage (13), which authorize said transfer of the temperature measurement only if the difference between the two voltages does not exceed a predetermined value.

7. An apparatus according to claim 6, characterized in that it comprises display means (8, 9 and 10) actuated by the fertility computer (7) for indicating after the temperature measurement the state of fertility of the person.

8. An apparatus according to claim 7, characterized in that the contact detector (2) is further coupled in circuit for initiating operation of the means (13, 14) for controlling the voltage of the power supply, of the controller (3) and of the display means (8, 9, 10) and in that the time controller (20, 23) is further coupled in circuit for initiating the temperature measurement and the operation of the fertility calculator (17), and for stopping of the operations of the means for controlling the voltage of the power supply and the display means initiated by the contact detector (2) for putting the apparatus in non working condition as soon as the person interrupts the contact of the probe (1) with the body.

9. Apparatus according to claim 1, characterized in that it comprises means for assuring that, in case of omission of at least one daily temperature measurement, temperature measurements on subsequent days continue on the basis of the temperature measurements following and preceding the at least one omitted measurement.

10. Apparatus according to claim 1, characterized in that it is provided with means for assuring that, if the electric power supply becomes non-operating during a short duration (for example 90 seconds), on the one hand the data memorized in the apparatus are preserved, and, on the other hand, the next temperature measurement following said short duration acts as a new start, independent of the last automatic assignment of the position in time of the time window of the following day, to enable the user to adapt to a change of time.

* * * * *